(12) United States Patent
Nashed (10) Patent No.: US 8,336,549 B2
(45) Date of Patent: Dec. 25, 2012

(54) DISPOSABLE ANESTHESIA FACE MASK

(76) Inventor: Ramses Nashed, Tierra Verde, FL (US)

(*) Notice: Subject to any disclaimer, the term of this patent is extended or adjusted under 35 U.S.C. 154(b) by 696 days.

(21) Appl. No.: 11/809,435

(22) Filed: Jun. 1, 2007

(65) Prior Publication Data

US 2007/0295335 A1 Dec. 27, 2007

Related U.S. Application Data

(63) Continuation-in-part of application No. 11/529,617, filed on Sep. 28, 2006, now abandoned, which is a continuation of application No. 10/922,472, filed on Aug. 20, 2004, now Pat. No. 7,114,498, which is a continuation-in-part of application No. 10/747,638, filed on Dec. 29, 2003, now Pat. No. 7,004,163, application No. 11/809,435, which is a continuation-in-part of application No. 11/363,014, filed on Feb. 27, 2006, now abandoned, which is a continuation-in-part of application No. 10/922,472, filed on Aug. 20, 2004, now Pat. No. 7,114,498, which is a continuation-in-part of application No. 10/747,638, filed on Dec. 29, 2003, now Pat. No. 7,004,163.

(51) Int. Cl.
*A62B 18/02* (2006.01)
*A61M 15/00* (2006.01)
*A61M 16/10* (2006.01)

(52) U.S. Cl. ......... 128/206.28; 128/200.24; 128/203.29; 128/205.25; 128/206.21; 128/203.12

(58) Field of Classification Search .................. 128/857, 128/863, 200.24, 201.22, 201.23, 201.25, 128/201.28, 202.27, 203.12, 203.13, 203.14, 128/203.29, 204.18, 204.21, 205.25, 206.12, 128/206.21, 206.24, 206.27, 206.28, 206.29, 128/207.11, 207.12, 910–914

See application file for complete search history.

(56) References Cited

U.S. PATENT DOCUMENTS

| | | | | | |
|---|---|---|---|---|---|
| 2,875,757 | A | * | 3/1959 | Galleher, Jr Ellis A | .. 128/206.26 |
| 3,695,264 | A | * | 10/1972 | Laeral | ...... 128/202.28 |
| 3,769,966 | A | * | 11/1973 | Youdin et al. | ................ 600/431 |
| 4,226,234 | A | * | 10/1980 | Gunderson | ............. 128/205.24 |
| 4,537,190 | A | * | 8/1985 | Caillot et al. | ............ 128/204.22 |
| 4,807,617 | A | * | 2/1989 | Nesti | ........................ 128/205.12 |
| 4,903,693 | A | * | 2/1990 | Yasue | ...................... 128/203.12 |
| 5,265,595 | A | | 11/1993 | Rudolph | |
| 5,400,781 | A | * | 3/1995 | Davenport | .............. 128/206.28 |
| 5,465,712 | A | * | 11/1995 | Malis et al. | .............. 128/205.25 |
| 5,474,060 | A | * | 12/1995 | Evans | ..................... 128/204.22 |
| 5,738,094 | A | * | 4/1998 | Hoftman | .................. 128/206.26 |
| 5,975,079 | A | | 11/1999 | Hellings et al. | |

(Continued)

OTHER PUBLICATIONS

Salter Labs—"Nasal Cannula"—2 pgs.

(Continued)

*Primary Examiner* — Annette Dixon
(74) *Attorney, Agent, or Firm* — Ronald E. Smith; Smith & Hopen, P.A.

(57) ABSTRACT

A disposable anesthesia face mask comprising a shell member having an annular flange and a do-nut shaped pneumatic sealing cushion attached to the shell member annular flange. The shell member and its flange are "pear-shaped" defining a nasal portion of first transverse extent, a mouth portion of second transverse extent, and an under-the-chin engagement portion of third transverse extent where the second transverse extent is greater than the first transverse extent and the third transverse extent is greater than the second transverse extent.

4 Claims, 8 Drawing Sheets

U.S. PATENT DOCUMENTS

| | | | | |
|---|---|---|---|---|
| 6,035,852 A * | 3/2000 | Hoftman | .................. | 128/206.26 |
| 6,263,874 B1 | 7/2001 | LeDez et al. | | |
| 6,273,087 B1 * | 8/2001 | Boussignac et al. | ..... | 128/204.22 |
| 6,357,437 B1 * | 3/2002 | Jacques | .................... | 128/201.25 |
| 6,408,853 B1 * | 6/2002 | Chang | .......................... | 128/857 |
| 6,534,769 B1 * | 3/2003 | Graham | ....................... | 250/343 |
| 6,860,268 B2 * | 3/2005 | Bohn et al. | ............... | 128/206.21 |
| 7,004,163 B2 * | 2/2006 | Nashed | .................... | 128/201.22 |
| 7,004,168 B2 * | 2/2006 | Mace et al. | .............. | 128/206.21 |
| 7,114,498 B1 * | 10/2006 | Nashed | .................... | 128/205.27 |
| 7,243,649 B2 | 7/2007 | Moenning et al. | | |
| 2001/0025641 A1 * | 10/2001 | Doane et al. | ............. | 128/207.15 |
| 2004/0084048 A1 | 5/2004 | Stenzler et al. | | |
| 2008/0295845 A1 * | 12/2008 | Nashed | .................... | 128/206.26 |

OTHER PUBLICATIONS

Capnoxygen®—"Oz Mask"—1 pg.

Koo Americas- "Face Mask"—2 pgs.

"Injury and Liability, etc." Bhanankar et al, Anesthesiology 2006; 104:228-34.

* cited by examiner

DISPOSABLE ANESTHESIA FACE MASK

RELATED APPLICATIONS

The present application is a continuation-in-part (CIP) of my prior pending U.S. patent application Ser. No. 11/529,617, filed Sep. 28, 2006, which, in turn, is a continuation (CON) of my yet prior U.S. patent application Ser. No. 10/922,472, filed Aug. 20, 2004 (now U.S. Pat. No. 7,114,498), which latter, in turn, is a continuation-in-part (CIP) of my still yet prior U.S. patent application Ser. No. 10/747,638, filed Dec. 29, 2003 (now U.S. Pat. No. 7,004,163).

This application also is a continuation-in-part (CIP) of my prior pending application U.S. application Ser. No. 11/363,014, filed Feb. 27, 2006 which is a continuation-in-part (CIP) of my prior U.S. patent application Ser. No. 10/922,472, filed Aug. 20, 2004, which, in turn is a continuation-in-part (CIP) of my still prior U.S. patent application Ser. No. 10/747,638, filed Dec. 29, 2003 (now U.S. Pat. No. 7,004,163).

Each of my aforesaid prior patent applications is incorporated herein and made part hereof by this reference.

BACKGROUND OF THE INVENTION

1. Field of the Invention

As disclosed in my prior pending applications, Ser. No. 11/529,617, filed Sep. 28, 2006, and Ser. No. 11/363,014, filed Feb. 27, 2006, the present invention relates generally to gas delivery, evacuation and respiratory monitoring systems and methods and more particularly pertains to allowing a user to deliver at least one gas and scavenge the exhausted gas as well as monitor the exhausted gas in a safe and efficient manner. A preferred use for such system and method is the application of anesthesia gas(es) to a patient undergoing surgery. Even more particularly, the present invention relates to new and improved disposable anesthesia face masks which may be used in such systems and methods.

2. Description of the Prior Art

The use of face masks to apply inhalation agents (gases) is well known in the medical treatment art. For example, during the administration of general anesthesia (GA) it is common to ventilate a patient with oxygen during the pre-intubation stage (induction) using a mask coupled to a suitable supply. Sometimes it is necessary to continue to use mask ventilation during surgery when a patient cannot be intubated with an endo-tracheal tube, or during procedures of relatively brief duration. On other occasions, it may be desirable to provide supplemental anesthesia using various anesthesia inhalation agents in the form of a gas selected, for example, from the group consisting of desflurane, sevoflurane, isoflurane, or nitrous oxide, or combinations thereof. Oxygen or the inhalation gas(es) selected by the anesthesia provider typically are applied to a patient using an inhalation face mask connected to a tube or tubes (such tubes commonly being referred to as a breathing circuit) which in turn is connected to a suitable gas supply. Generally, once a patient is ventilated and then intubated with an endo-tracheal tube or the like, the mask is set aside until the end of the procedure when the endo-tracheal tube is removed and the patient briefly is ventilated with O2 through the mask. Exemplary of gas inhalation masks used in administering GA to a patient is that disclosed in U.S. Pat. No. 5,975,079 (Hellings et al). As indicated by this patent, an acceptable anesthesia mask should be disposable, made of transparent material, have a strap or straps to hold the mask in place when desired, be of sufficient size to cover the patient's nose and mouth, and have a pneumatic sealing cushion, not only to promote patient comfort, but to prevent exposing anesthesia or other personnel to the applied gas or gases. This patent (U.S. Pat. No. 5,975,079) hereby is incorporated herein and made part hereof by this reference.

In my prior pending U.S. patent application Ser. No. 11/529,617, filed Sep. 28, 2006, and Ser. No. 11/363,014, filed Feb. 27, 2006, I disclose and claim a face mask which is capable of functioning as an improved anesthesia mask compared to the prior art masks (exemplified by the '079 patent) because my mask in accordance with my inventive concept(s) uniquely combines the following advantages, inter alia: (1) the ability to deliver and evacuate gas(es) while being sealed on the patient's face, (2) the provision of an end-tidal CO2 monitoring port directly on the mask itself in a location promoting extremely accurate CO2 signal tracing and readout, and further, (3) the provision of a mask face having a bottom or basal portion adapted to engage the underside of the chin or jaw of the wearer or patient in such a way as to stabilize the mask on the patient's face without affecting its sealing capability.

During the application of general anesthesia (GA), it has become standard practice to always monitor the patient to assure proper breathing. One way to accomplish this is to detect CO2 present in exhaled air or end-tidal breathing of the patient. This may be done efficiently by providing an end-tidal CO2 port on the breathing circuit attached to the mask or to the endo-tracheal tube and connecting a flexible tube between the port and a device (capnograph) for monitoring end-tidal CO2.

In surgical cases where monitored anesthesia care (MAC) is employed, the patient merely is sedated rather than being paralyzed and intubated (as in GA). It is known to monitor end-tidal CO2 in such cases (MAC) sporadically by employing nasal cannula connected to a capnograph, or by using an oxygen mask with a CO2 sampling tube. For example, a divided-cannula with an O2 line and a CO2 line is commercially distributed by Salter Labs, Arvin, Calif. whereas an oxygen mask with a CO2 sampling tube is commercially distributed by Southmedic under the Capnoxygen® trademark. The failure to efficiently monitor end-tidal CO2 during MAC anesthesia can have adverse medical reactions. Bhananker et al have reported in "*Injury and Liability Associated with Monitored Anesthesia Care,*" *Anesthesiology* 2006, 104: 228-34, incorporated herein by this reference, that nearly half the claims studied "were judged as preventable by better monitoring including capnography and that patient safety during MAC may be improved by the use of capnography."

Prior masks used in general anesthesia are designed to cover only the nose and mouth, and therefore (unlike the present invention), the capability of using the patient's chin to anchor and stabilize the anesthesia mask has gone unrecognized. In fact, as disclosed in the '079 patent, when an anesthesia mask of limited extent (i.e. sized and configured to cover only the nose and mouth) is applied to a patient's face, the mask is unstable and must be held in position by hand. Only when a relatively complicated and unwieldy strap or headband assembly is employed to affix the mask in place are anesthesia personnel free to use both hands (see column 2, lines 3-5, in the '079 patent). Even so, because the mask is covering only the nose and mouth of the patient's face such headbands must be applied with a relatively high tension or tightening force to maintain an effective seal. Accordingly, such masks are poorly tolerated by sedated patients and when tightened on a patient's face or head in order to be stabilized, the danger of injury to facial or ocular tissue is presented. Hence, to applicant's knowledge, these masks have not been employed during MAC procedures. By anchoring a sealable mask at the chin (as is disclosed only in my prior application Ser. Nos. 11/363,014 and 11/529,617), the mask is rendered stable and displacement toward the ocular area or elsewhere is prevented under virtually all conditions likely to be encountered during the ensuing surgical procedure. Moreover, a relatively simple headband (elastic) that engages only the periphery of the mask may be employed without excessive pressure and anesthesia personnel do not have to be concerned about also holding the mask in place on the patient's face thereby freeing both hands to attend to other important tasks.

Although the mask disclosed and claimed in my prior application Ser. Nos. 11/363,014 and 11/529,617, overcomes many of the disadvantages of prior art masks particularly with respect to providing chin engagement stability and end-tidal $CO_2$ monitoring capability in a sealable face mask capable of delivering and evacuating gases(s), this form of anesthesia mask is susceptible of still further improvements and refinements not shown nor suggested in the prior art.

Therefore, it can be appreciated that there exists a continuing need for a new and improved disposable anesthesia face mask for use in providing inhalation gas(es) to a patient in the context of a gas delivery, evacuation and respiratory monitoring system and in this regard, the present invention substantially fulfills this need.

BRIEF SUMMARY OF THE INVENTION

In view of the foregoing disadvantages inherent in the known masks now present in the prior art, the present invention provides an improved disposable anesthesia mask which will be described subsequently in greater detail, and whose general purpose is to provide such a mask which has all the advantages of the prior art and none of the disadvantages.

To attain this, the present invention, briefly described, essentially comprises a face mask suitably sized and configured to engage the nose portion, mouth portion and chin portion of a patient's face. The face mask of the present invention has two primary components, namely a cup-like shell or receptacle member terminating at its peripheral edge in a circumferential flange, and an annular donut-shaped hollow inflatable cushion or seal member affixed or otherwise permanently attached to the flange. The shell member preferably is transparent to permit viewing therethrough. The shell member is shaped suitably to define a nose reception portion, a mouth reception portion, and a chin reception portion, and includes first passageway means extending from the shell member in a direction opposite to the terminating flange for coupling to a breathing circuit, and has a second passageway preferably also extending in a direction opposite to the terminating flange for connection to a flexible tube which, in turn, is adapted to be connected to a $CO_2$ monitoring machine or capnograph. The face mask nasal portion has a first width, the face mask mouth portion has a second width greater than the first width, and the face mask chin portion has a third width greater than the second width, giving the face mask shell a characteristic pear-shaped configuration. The nasal, mouth and chin portions are continuous and form the cup-like extent of the shell or receptacle component. The mask has lateral projections on the flange for accommodating a suitable elastic head strap that may adjustably be coupled to the projections to hold the mask in place on a patient's face and head.

There has thus been outlined, rather broadly, several important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved face mask suitable for use with a gas delivery, evacuation and respiratory monitoring system which face mask has all of the advantages of the prior art face masks and none of the disadvantages.

It is another object of the present invention to provide a new and improved face mask that especially suitable for use in applying anesthesia inhalation gas or gases to a patient.

It is further object of the present invention to provide a new and improved disposable anesthesia face mask which is of durable and reliable constructions.

An even further object of the present invention is to provide a new and improved disposable anesthesia face mask which is susceptible of a low cost of manufacture with regard to both materials and labor, and which accordingly is then susceptible of low prices of sale, thereby making such a face mask economically available to the medical community.

Even still another object of the present invention is to provide a new and improved disposable anesthesia face mask that may be used on a patient before and during surgery in a safe and efficient manner.

It is yet another object of the present invention to provide a new and improved disposable anesthesia face mask suitably sized and configured to engage the nose portion, mouth portion and chin portion of a patient's face.

Still yet another object of the present invention is to provide a new and improved disposable anesthesia face mask characterized by two primary components, namely a cup-like shell or receptacle member terminating at its peripheral edge in a circumferential flange, and an annular donut-shaped hollow inflatable cushion or seal member affixed or otherwise permanently attached to the flange and wherein the shell member preferably is transparent to permit viewing therethrough.

Another object of the present invention is to provide a new and improved disposable anesthesia face mask characterized by two primary components, namely a cup-like shell or receptacle member terminating at its peripheral edge in a circumferential flange, and an annular donut-shaped hollow inflatable cushion or seal member affixed or otherwise permanently attached to the flange and which further includes lateral projections on the flange for accommodating a head strap that may be suitably coupled to the projections to hold the mask in place on a patient's face and head.

It is yet still another object of the present invention to provide a new and improved disposable anesthesia face mask suitably sized and configured to engage the nose portion, mouth portion and chin portion of a patient's face, wherein the face mask has two primary components, namely a cup-like shell or receptacle member terminating at its peripheral edge in a circumferential flange, and an annular donut-shaped hollow inflatable cushion or seal member affixed or otherwise permanently attached to the flange, wherein the shell member preferably is transparent to permit viewing therethrough, wherein the shell member is shaped suitably to define a nose reception portion, a mouth reception portion, and a chin reception portion, and includes first passageway means extending from the shell member in a direction opposite to the terminating flange for coupling to a breathing circuit, and wherein the shell member has a second passageway preferably also extending in a direction opposite to the terminating flange for connection to a flexible tube which, in turn, is adapted to be connected to a CO2 monitoring machine or capnograph, wherein the face mask nasal portion has a first width, the face mask mouth portion has a second width greater than the first width, and the face mask chin portion has a third width greater than the second width giving it a characteristic "pear" shape, wherein the nasal, mouth and chin portions are continuous and form the cup-like extent of the shell or receptacle component, and wherein the mask has lateral projections on the flange for accommodating a head strap that may be suitably coupled to the projections to hold the mask in place on a patient's face and head.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
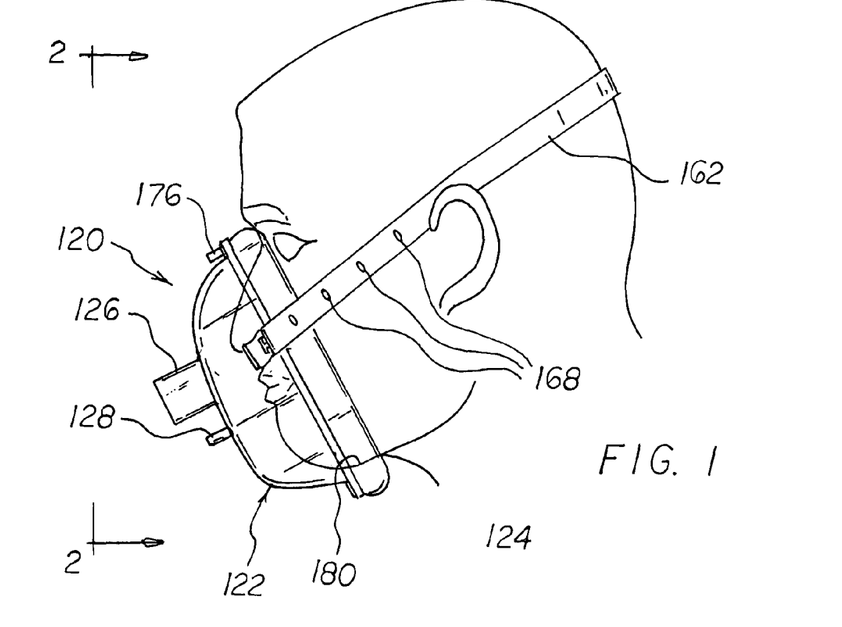
FIG. 1 is a side elevational view of disposable anesthesia mask of the present invention in position on a patient's face.
Figure 2:
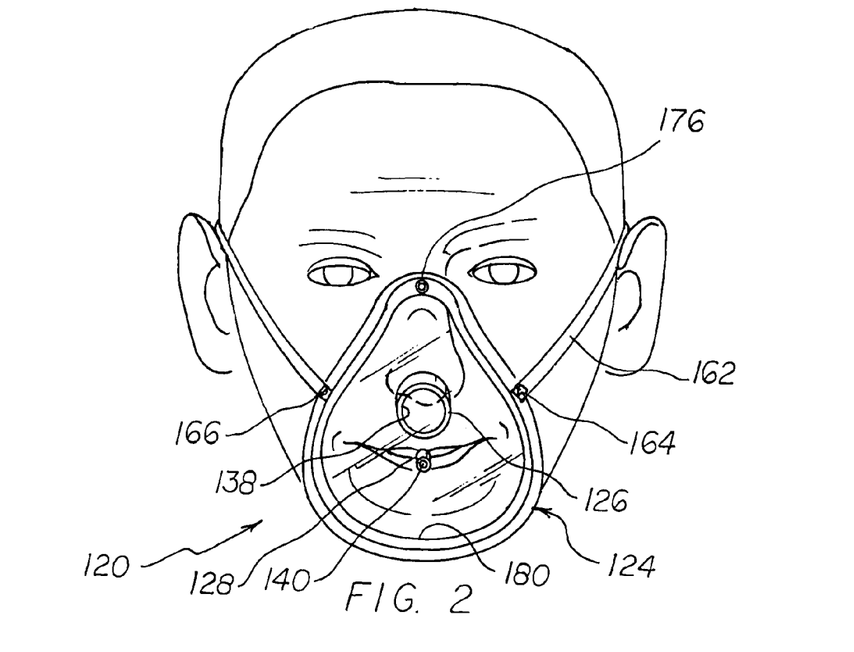
FIG. 2 is a front elevational view of the mask shown in FIG. 1.

With reference now to the drawings, and initially to FIGS. 1-6 and 15-16 thereof, the preferred embodiment of the new and improved disposable anesthesia face mask embodying the principles and concepts of the present invention and generally designated by the reference numeral 120 will be described. Face mask assembly 120 comprises two primary components, a shell or receptacle member generally indicated by reference sign 122 and a pliable or flexible pneumatic (inflatable) cushion sealing member generally indicated by reference sign 124. Shell member 122 preferably is of one-piece or unitary construction fabricated in a known manner from a synthetic polymeric resin such as polyvinyl chloride, for example, and is transparent so that when face mask 120 is worn on the face of a patient substantially as depicted in FIGS. 1 and 2, the portion of the patient's face covered by the mask is clearly visible at all times.

Shell member 122 has a first cylindrical hollow inlet member or port 126 of a first outside diameter and a second cylindrical hollow outlet member or port 128 of a second outside diameter with inlet and outlet members 126, 128 protruding or extending from the outer or top wall portion 130 thereof (FIGS. 1, and 4-6). The first diameter of outlet member 126 is greater than the second diameter of inlet member 128. Moreover, the height of inlet member 126 above top wall portion 130 is greater than the height of outlet member 128 above top wall portion 130. In accordance with the invention, port members 126, 128 are located centrally on the imaginary main axis 132 of shell member 122 (and face mask 120) with outlet member 128 being spaced from inlet member 126 a distance "D" (FIG. 3) substantially as depicted.

The outer or top wall portion 130 of shell member 122 extends slopingly into a continuous sidewall portion 134 all along the peripheral extent of the shell member. The top wall portion 130 and continuous sidewall 134 of shell member 122 are concave defining in accordance with the invention a generally pear-shaped cup-like receptacle having an interior cavity 136 defined by the inner convex surface 138 of top wall portion 130 and continuous sidewall portion 134. As will be explained in more detail below, and further in accordance with the present invention, pear-shaped interior cavity 136 is suitably shaped and sized to receive the nose portion, mouth portion and chin portion of a patient's face when the face mask assembly 120 is sealingly applied to that patient's face.

Figure 15:
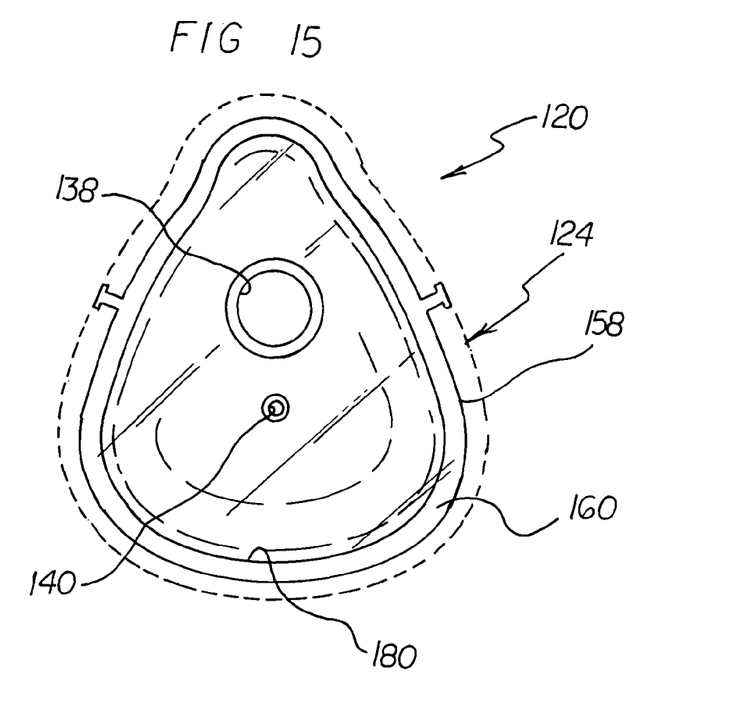
FIG. 15 is a bottom plan view of the mask of FIG. 1 with the pneumatic cushion member thereof being shown in broken lines to avoid obfuscation.
Figure 16:
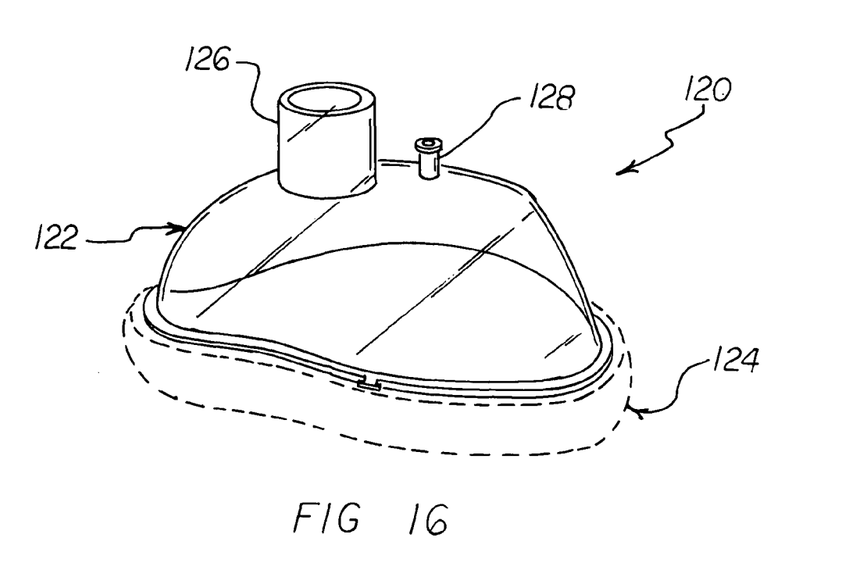
FIG. 16 is a schematic perspective view of the mask of FIG. 1 with the pneumatic cushion member thereof being shown in broken lines to avoid obfuscation and showing the characteristic "pear" shape of the mask's shell member.

The characteristic pear-shape of the mask shell member 122 is further clearly shown in FIGS. 15 and 16.

Figure 3:
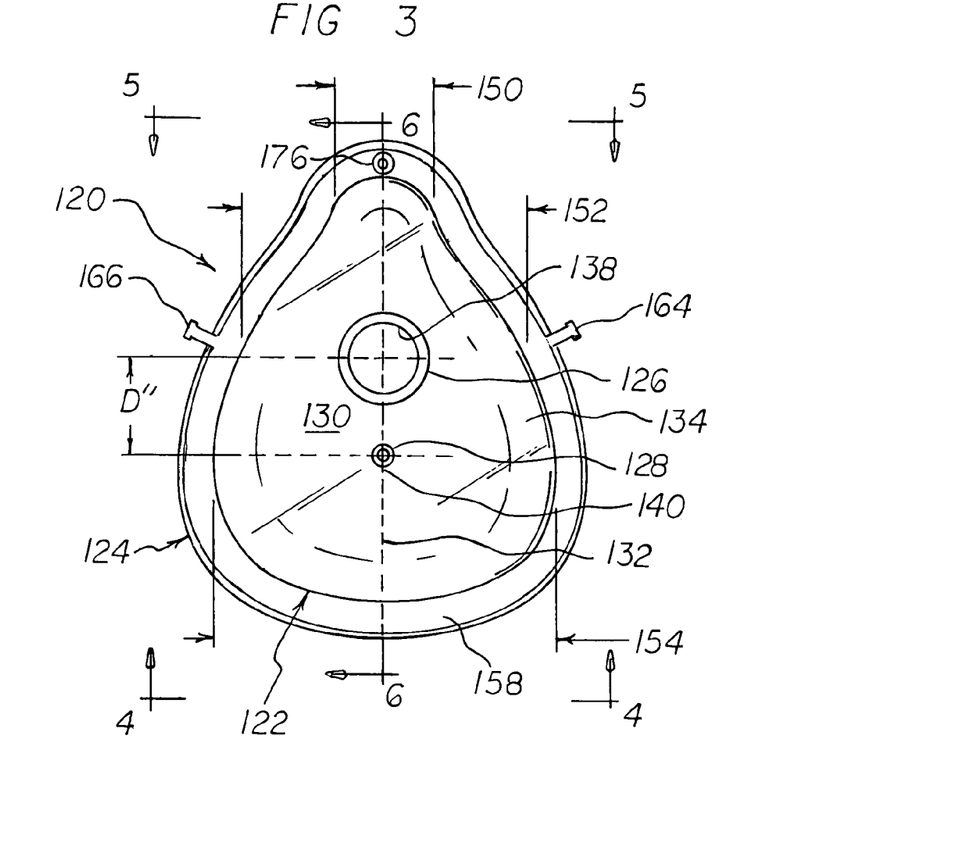
FIG. 3 is a top plan view of the mask of FIG. 1.
Figure 4:
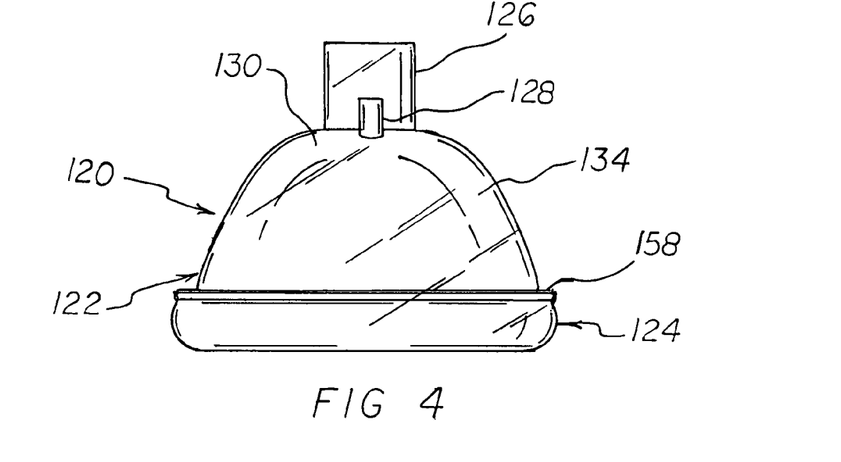
FIG. 4 is an elevational view of the bottom of the face mask of FIG. 1.
Figures 5, 6, 6A:
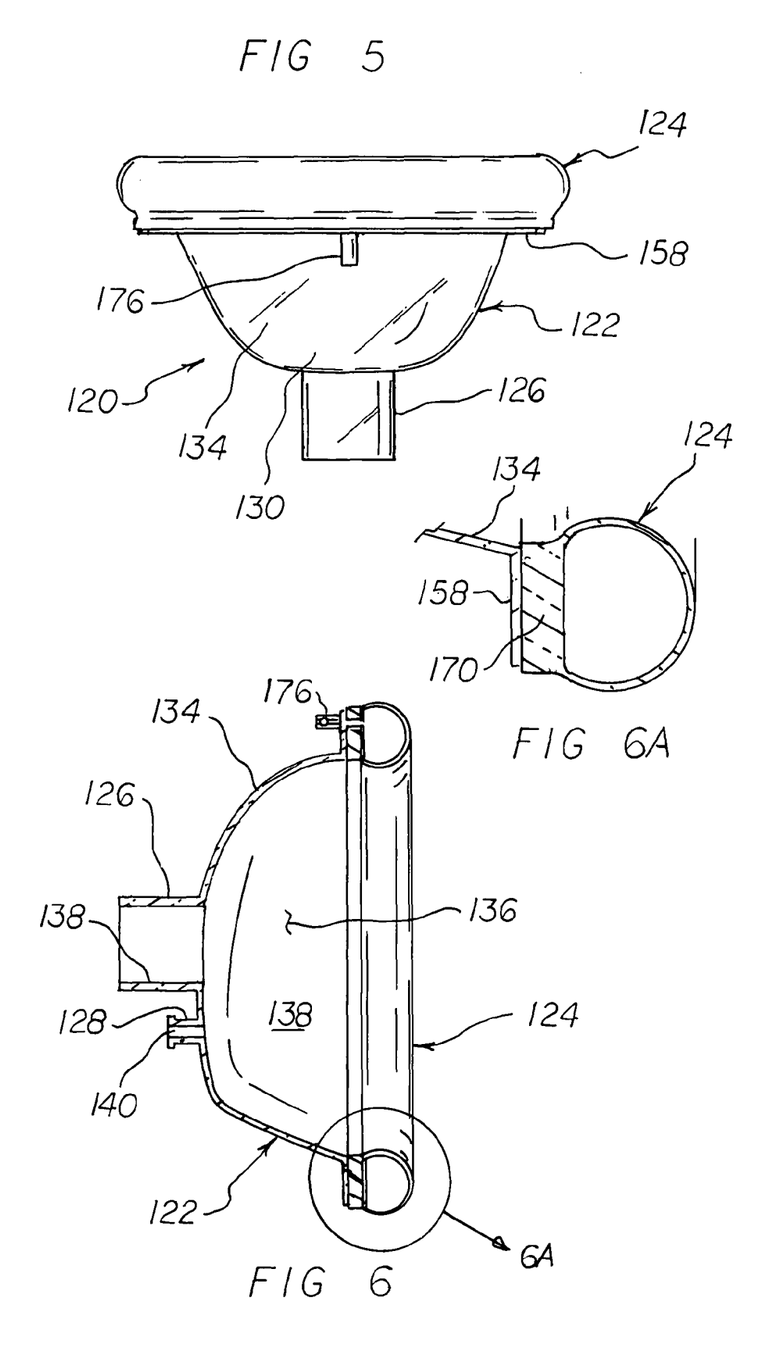
FIG. 5 is an elevational view of the top of the mask of FIG. 1.
FIG. 6 is a cross-sectional view of the mask of FIG. 3 taken along line 6-6.
FIG. 6A is an enlarged view of the portion of the mask shown in the circle in FIG. 6.
Figure 12:
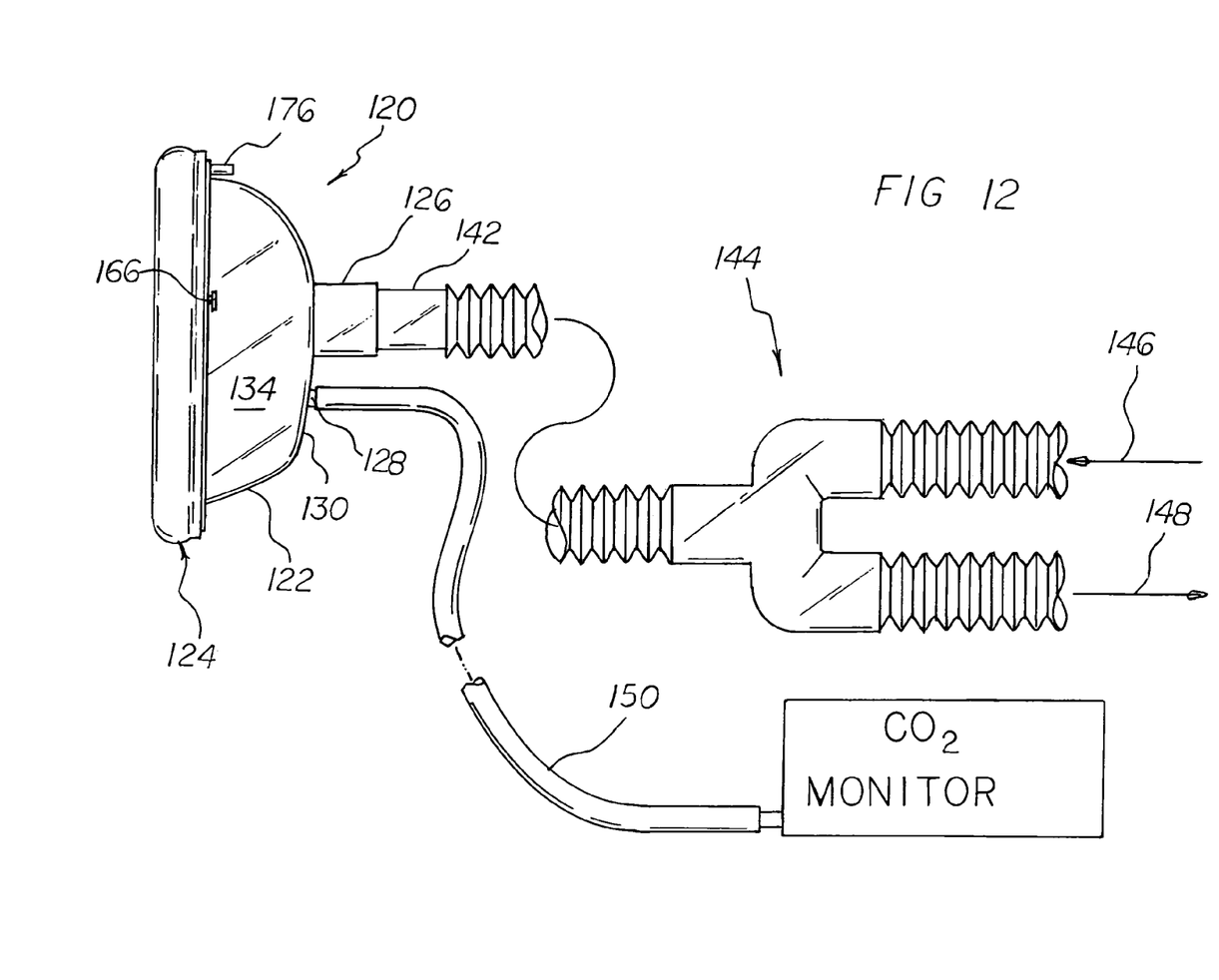
FIG. 12 is a schematic diagram showing the mask of the present invention attached to a breathing circuit and to an End Tidal CO2 monitor (capnograph) through a flexible tube.
Figure 13:
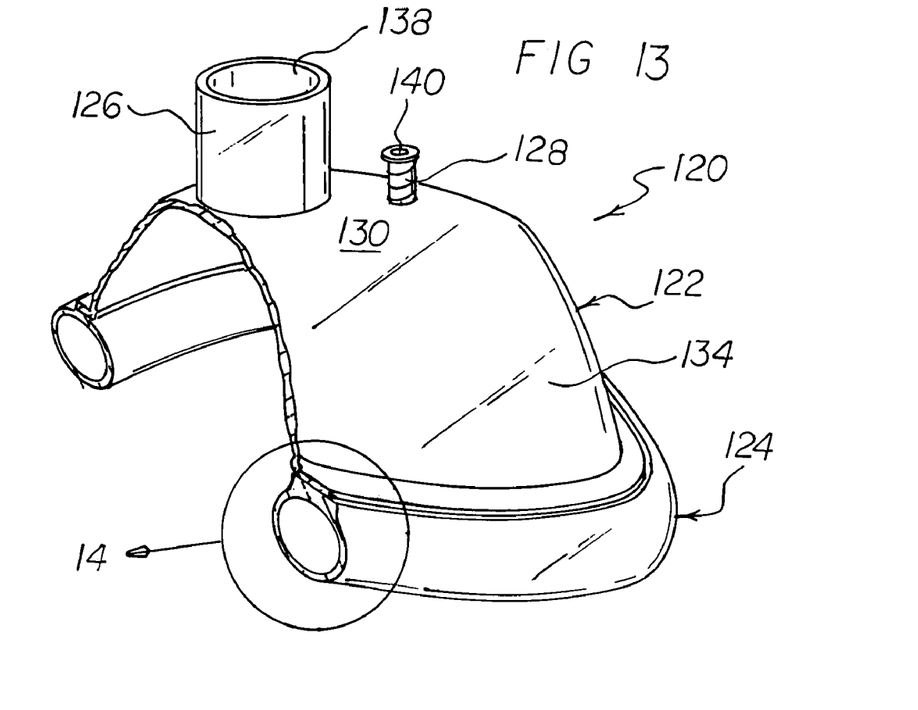
FIG. 13 is a fragmentary perspective view of a portion of the mask according to the invention showing how the sealing cushion is attached to the shell component's flange.

As best viewed in FIGS. 3, 6, and 15, hollow inlet member or port 126 defines a first passageway 138 opening into interior cavity 136 whereas second outlet member or port 128 defines a second passageway 140 opening into interior cavity 136. As schematically illustrated in FIG. 12, passageway 138 is suitably sized to receive in snug sliding (and sealing) engagement therein the nipple 142 of a conventional two-branch breathing circuit 144 such that anesthesia gas or gases are adapted to pass from a source (not shown) through one branch of the breathing circuit 144 through passageway 138 into the interior cavity 136 of shell member 122 (and mask 120) as indicated by arrow 146. The breathing circuit 144 also is adapted to receive returned exhaust gas or gases through the same passageway 138 via nipple 142 and convey such exhausted gas or gases in a second branch as indicated by arrow 148 when the second branch is connected to a conventional gas evacuation or scavenging apparatus (not shown). The outside diameter of outlet member 128 suitably is sized to have snugly (and sealingly) fitted thereon one end of a flexible tube 150 the other or distal end of which is adapted suitably to be connected to a conventional $CO_2$ monitoring device or capnograph substantially as schematically depicted in FIG. 12. The $CO_2$ outlet member 128 may include a suitable screw-on type cap or closure member (not shown) when not being used.

In accordance with an important feature of the present invention, the location of cylindrical ports 126 and 128 on shell member 122 is such that when the mask assembly 120 suitably is fitted to a patient's face, passageway 138 of inlet member 126 is located proximal to the patient's nasal region whereas passageway 140 of outlet member 128 is located proximal to the mouth region of the patient. This relationship is clearly shown in FIGS. 1 and 2. Surprisingly, I have found that when the $CO_2$ monitoring or sampling tube is coupled to and positioned on shell member 122 is such a manner, end-tidal breathing of the patient impinges directly on the inlet of passageway 140 within cavity 136 and this in turn, produces an extremely accurate high-magnitude readout or trace of sensed $CO_2$ on the capnograph display and audio alarm. In prior art anesthesia mask arrangements employing a sealing cushion, the $CO_2$ monitoring tube typically is coupled to the breathing circuit at a location downstream of the mask and thereby produces a weaker, less accurate and sometimes even an erratic $CO_2$ signal readout on the capnograph.

As best seen in FIGS. 1, 3, 6, 15 and 16, shell member 122 when projected in the plane of the paper of FIG. 3 (and see also FIG. 16) essentially appears pear-shaped with a first transverse width or extent 150 at the top thereof defining the nose reception region of the mask 120, a second or intermediate transverse width or extent 152 defining the mouth reception region of the mask 122, and at the bottom thereof, a third transverse width or extent 154 defining the chin or jaw reception region of the mask 122 with the third extent 154 being greater than the intermediate extent 152 and the intermediate extent 152 being greater than the first transverse extent 150. Continuous sidewall portion 134 of shell member 122 which extends along the entire peripheral extent of the shell member 122 terminates in a radially outwardly extending flange member 158 which defines on the bottom thereof a pneumatic sealing cushion mounting surface 160. Flange member 158 is substantially flat such that bottom surface 160 lies in an imaginary plane substantially normal to the imaginary central axes of port members 126 and 128 (FIGS. 1, 4, 6 and 7). This feature enables the shell member 122 to be easily and relatively inexpensively fabricated as by injection molding, for example, and surprisingly further enables the mask readily to be attached to the head of the patient using a relatively simple elastic headband or strap member 162 selectively attachable to the mask shell 122 preferably by way of a pair of protruding integral T-shaped posts 164, 166 extending oppositely and radially from the flange 158 respectively, substantially as shown in FIG. 3 and elsewhere in the drawings. The elastic strap member 162 preferably includes a series of spaced holes 168 which are adapted easily to be engaged by the T-shaped posts 164, 166 when it is desired to fasten the head strap and mask assembly 120 about the head of a patient in a manner believed obvious to a person of ordinary skill. Because the mask assembly 120 is adapted to be fitted to the patient's face with the chin portion of the face being received in the cavity 136 near the bottom of mask assembly 120 (FIG. 1), and further because the T-shaped posts 164, 166 are located on the flange member 158 upwardly near the nose portion of the mask assembly 120 substantially as illustrated in FIGS. 1-3, the tension in the elastic headband 162 when so attached provides an extremely stable suspension system securely maintaining the mask assembly in place before or during surgery and enabling anesthesia personnel to attend to other tasks using both hands free.

Figure 7:
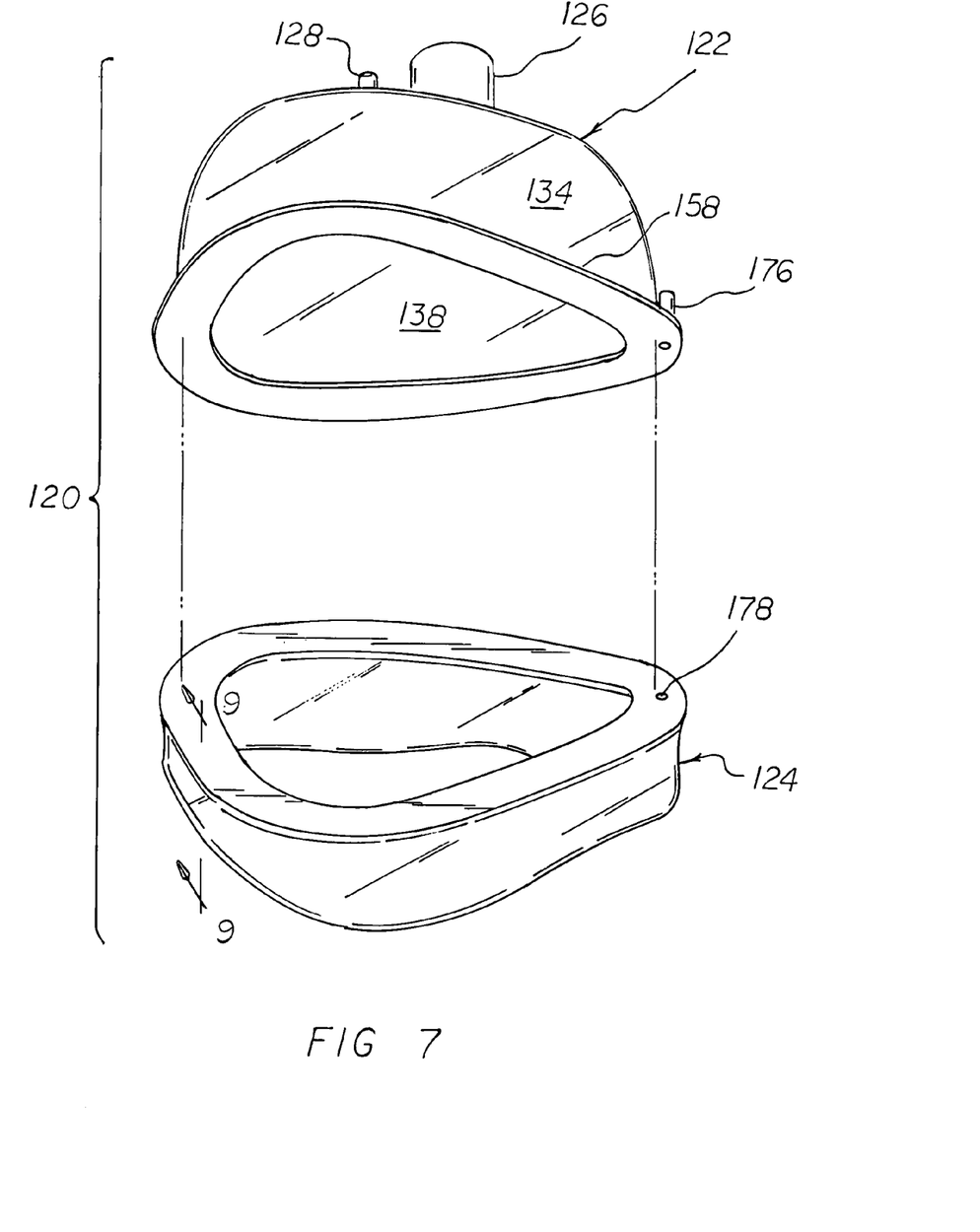
FIG. 7 is an exploded assembly of the mask of FIG. 1 showing the shell component and the flexible annular sealing cushion component.

Suitably affixed to the mounting surface 160 on flange 158 is the pneumatic sealing cushion 124 which essentially comprises an inflatable donut-shaped hollow annular member made of pliable flexible material, preferably 7). This feature enables the shell member 122 to be easily and relatively inexpensively fabricated as by injection molding, for example, and surprisingly further enables the mask readily to be attached to the head of the patient using a relatively simple elastic headband or strap member 162 selectively attachable to the mask shell 122 preferably by way of a pair of protruding integral T-shaped posts 164, 166 extending oppositely and radially from the flange 158 respectively, substantially as shown in FIG. 3 and elsewhere in the drawings. The elastic strap member 162 preferably includes a series of spaced holes 168 which are adapted easily to be engaged by the T-shaped posts 164, 166 when it is desired to fasten the head strap and mask assembly 120 about the head of a patient in a manner believed obvious to a person of ordinary skill.

Because the mask assembly 120 is adapted to be fitted to the patient's face with the chin portion of the face being received in the cavity 136 near the bottom of mask assembly 120 (FIG. 1), and further because the T-shaped posts 164, 166 are located on the flange member 158 upwardly near the nose portion of the mask assembly 120 substantially as illustrated in FIGS. 1-3, the tension in the elastic headband 162 when so attached provides an extremely stable suspension system securely maintaining the mask assembly in place before or during surgery and enabling anesthesia personnel to attend to other tasks using both hands free.

Figure 14:
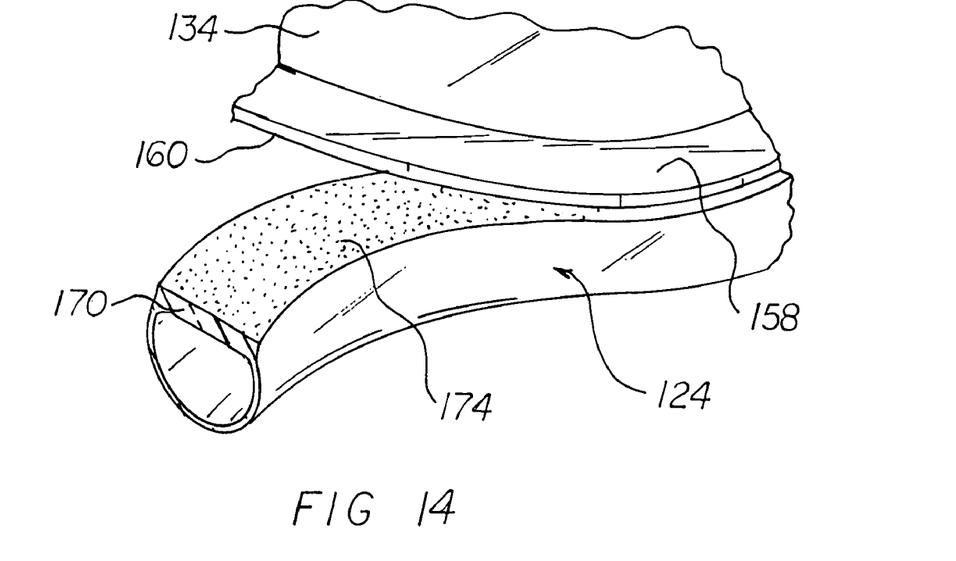
FIG. 14 is an enlarged detail of the portion of the mask shown in circle 14 of FIG. 13 with a portion of the sealing cushion being shown pulled away from the shell flange to more clearly illustrate the attaching surface on the sealing cushion.

Suitably affixed to the mounting surface 160 on flange 158 is the pneumatic sealing cushion 124 which essentially comprises an inflatable donut-shaped hollow annular member made of pliable flexible material, preferably synthetic polymeric resin such as polyvinyl chloride, for example. As shown in FIG. 6A, cushion member 124 preferably is formed with a somewhat thickened top wall portion defining a mounting foot or pad 170 which advantageously may be adhered securely to the mounting surface 160 of flange member 158 suitably by means of a compatible adhesive (indicated by stippling 174 in FIG. 14) or the like applied all along the top surface of pad 170, the mounting surface 160, or both. An inflation tube 176 with a conventional one-way check valve is provided on flange member 158 (FIG. 6) in registration with an opening 178 in pad 162 of cushion member 124 to facilitate selective inflation of the pneumatic cushion in a known manner.

Thus, when the mask assembly 120 is applied to the face of a patient in accordance with the present invention, it will be appreciated that the top of mask 122 receives and covers the nose portion of the patient, the intermediate portion of mask assembly 120 covers the mouth portion of the patient, and the bottom or widest inside edge portion 180 of mask assembly 120 receives and engages the underside of the chin and jaw portion of the patient's face substantially as depicted in FIG. 1 with the pneumatic sealing cushion member 124 effectively sealing the periphery of the mask assembly 120 relative to the patient's face preventing escape of anesthesia gas into the surrounding environment notwithstanding the irregular contour of the patient's face. In accordance with the invention, the foregoing engagement between the underside of the chin or jaw portion of the patient with the bottom or widest transverse edge portion 180 of mask assembly 120 prevents displacement of the mask toward the ocular area, helps to keep the patient's mouth closed, and securely stabilizes the mask assembly on the face when the elastic headband is used thereby freeing both hands of attending anesthesia personnel for use elsewhere.

Figure 8:
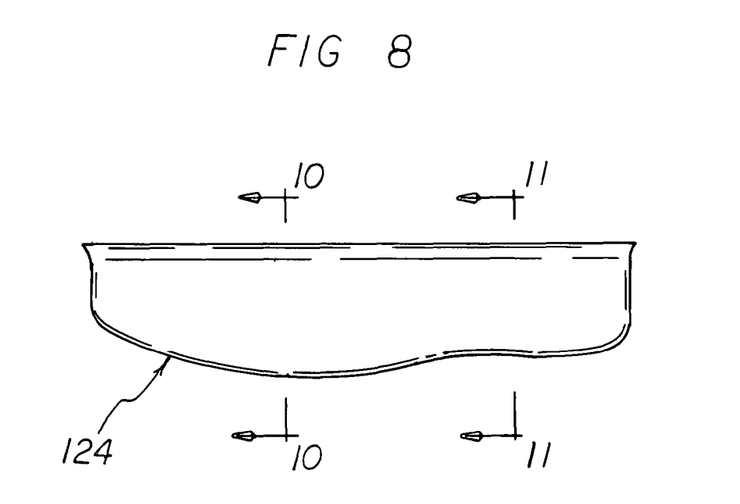
FIG. 8 is a side elevational view of the flexible annular sealing cushion component showing its variable contour.
Figure 9:
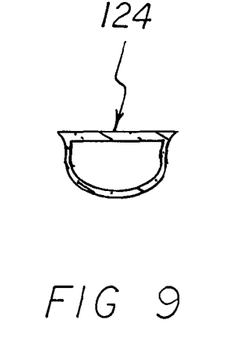
FIG. 9 is a cross-sectional view taken along line 9-9 of FIG. 7.
Figure 10:
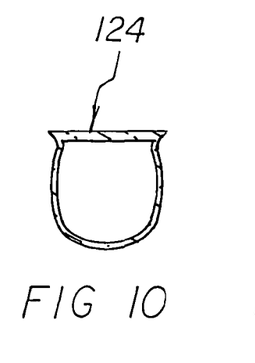
FIG. 10 is a cross-sectional view taken along line 10-10 of FIG. 8.
Figure 11:
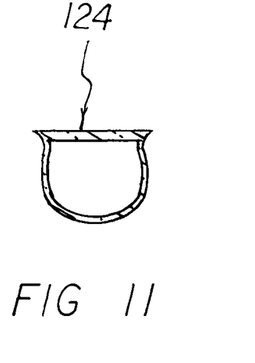
FIG. 11 is a cross-sectional view taken along line 11-11 of FIG. 8.

In order to facilitate an effective and comfortable fit of the pneumatic sealing cushion 124 and therefore the mask assembly 120 on the patient's face, the sealing cushion member 124 preferably has a variable contour. The term "variable contour" as used herein and in the annexed claims means a sealing cushion which when in the inflated condition has a different cross-sectional size, area or diameter at selected locations along its longitudinal extent, respectively. Thus, substantially as shown in FIGS. 7-11, sealing cushion 124 has a first diameter (or cross-sectional area) along the bottom of mask assembly 120 (FIGS. 7 and 9), a second diameter (or cross-sectional area) in the intermediate zone of the mask assembly (FIGS. 8 and 10), and a third diameter (or cross-sectional area) in the nasal region of the mask assembly (FIGS. 8 and 11). The foregoing resulting variable contour of the sealing cushion 124 advantageously enables mask assembly 120 to fit comfortably and effectively a wide range of patients using a single standard mask size. Fabrication of the resilient, hollow, inflatable sealing cushion 124 can be effected easily and relatively inexpensively using rotational molding techniques well known in the art.

It will be appreciated that the disposable anesthesia face mask of the present invention can be made in many different sizes (e.g. large adult, medium adult, small pediatric, large pediatric, and so on) so that virtually all patients may be fitted. Moreover, it will be appreciated with the mask of the present invention, a mask of one size category will fit many different patients in that category thus minimizing inventory and stocking challenges. Without limiting the present invention, and merely for the sake of illustration, a face mask assembly 120 according to the present invention suitable for use on an "average adult" may have the dimensions set forth in the following Table:

Height (measured above flat table to top of port 126)=3.25 inches.
Maximum transverse width in chin region not including flange=3.75 inches.
Intermediate transverse width in mouth region not including flange=3.5 inches.
Minimum transverse width in nose region not including flange=1 inch.
Length measured along main axis 132 including flange=6 inches.
Spacing "D" between port 126 and port 128=1.25 inches.
Height of main port 126 above flange top surface=1.25 inches.
Width of flange=0.375 inches.
Wall thickness of main port 126=0.25 inches.
Inside diameter of main port 126=0.875 inches.
Wall thickness of CO2 port=0.125 inches.
Inside diameter of CO2 port=0.25 inches.
Wall thickness of shell member 122 and flange=0.067 inches.
Height of inflated variable contour sealing cushion varies between 0.75 inches and 1.25 inches.
Diameter of inflated variable contour sealing cushion varies between 0.5 inches and 1.25 inches.
Nominal Wall thickness of inflated variable contour sealing cushion=0.0078 inches.

It will be appreciated from the foregoing that there is provided by the present invention a substantially new and improved disposable anesthesia face mask that can be efficiently used in GA and MAC procedures to provide for the delivery and evacuation of gas(es) while being sealed to the face, that provides accurate end-tidal CO2 monitoring capability, that is stable at all times on the face of the patient because the bottom or basal portion of the face mask engages the underside of the patient's jaw or chin, and that can be manufactured relatively easily and inexpensively making it widely and economically available to the medical community. In addition to these advantages, the following additional advantages are achieved by the novel disposable anesthesia mask disclosed and claimed herein:

(1) When used during GA, the mask of the present invention provides for an improved fit on and over the patient's face thus reducing the pressure or force needed to keep it in place.

(2) The mask of the present invention has superior ability to detect exhaled CO2 during GA induction (ventilation with O2) because of the location of the CO2 monitoring port proximal to the mouth and nose of the patient (this is especially true of patient's who tend to breath through their mouth).

(3) The mask of the present invention facilitates accurate monitoring of exhaled CO2 during MAC anesthesia.

(4) The mask of the present invention facilitates environmentally safe use of inhalation agents during MAC anesthesia without requiring the anesthesia provider to hold the mask in position on the patient's face.

(5) The mask of the present invention facilitates delivery of a higher concentration of O2 to a patient undergoing MAC compared to that capable of being delivered using prior art nasal cannula.

To use the disposable anesthesia face mask of the present invention, the anesthesia provider may conveniently grasp the mask shell in the left hand with the first passage member or port received between the thumb and forefinger and with the extremities of the third and fourth fingers extending over the bottom or widest edge of the mask assembly. Using the pinky on the provider's left hand, the patient's lower jaw may then be pulled upwardly while the mask is fitted to the patient's face, first by receiving the chin therein then by rotating downwardly onto the nose with slight pressure. This simple procedure promptly establishes and maintains a good seal preventing any leakage of anesthesia gases under suction (breathing). The mask assembly may then be attached to the patient's head by engaging selected openings in the headband with the strap projections on the mask shell.

As to any further manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A respiratory face mask for use on a user's face, comprising:
    a shell formed of transparent material;
    said shell having a top wall adapted to overlie said user's face when the mask is in use, said top wall being spaced apart from said user's face;
    a side wall having a first end formed integrally with said top wall about the periphery of said top wall, said side wall extending toward said user's face in a gradual bend and ending in a second end;
    a flange formed integrally with said second end of said side wall in circumscribing relation thereto, said flange extending radially outwardly relative to said shell to define a sealing cushion flange mounting surface proximal to said side wall second end, said sealing cushion flange mounting surface facing oppositely with respect to said top wall and being substantially coplanar throughout substantially its entire circumscribed extent;
    a flexible and resilient sealing cushion mounted on said flange mounting surface in circumscribing relation thereto, said sealing cushion adapted to sealingly engage said user's face in the region of the user's nose, mouth, and chin;
    said mask being generally pear-shaped and having a narrow first end adapted to fit over a user's nose;
    said generally pear-shaped face mask having a middle region adapted to fit over a user's mouth, said middle region having a breadth greater than said narrow first end;
    said generally pear-shaped face mask having a broad second end, said broad second end having a breadth greater than the breadth of said middle region, said broad second end of said pear-shaped face mask defining an under-the-chin engagement portion adapted to engage the underside of the user's chin or jaw when said narrow first end is fitted over said user's nose, said middle region fitting over said user's mouth when said sealing cushion is in engagement with said user's face in the region of the user's nose, mouth, and chin;
    said sealing cushion having a variable cross-sectional extent when viewed in side elevation with respect to said flange;
    said sealing cushion having a portion of first cross-sectional extent in said narrow first end, a portion of second cross-sectional extent in said middle region, and a portion of third cross-sectional extent in said broad second end;
    said sealing cushion portion of first cross-sectional extent being smaller than said sealing cushion portion of second cross-sectional extent; and
    said sealing cushion portion of third cross-sectional extent mounted on said flange forming a portion of said under-the-chin engagement portion defined by said broad second end on said pear-shaped face mask.

2. The face mask of claim 1, further comprising:
    a first port formed in said top wall, substantially centrally thereof;
    said first port adapted to releasably engage an elongate tube that forms a part of a breathing circuit.

3. The face mask of claim 2, further comprising:
    a second port formed in said top wall of said shell;
    said second port being a $CO_2$ port positioned below said first port so that end-tidal breathing of a patient impinges directly onto said $CO_2$ port;
    a remote $CO_2$ monitor
    said $CO_2$ post adapted to be in fluid communication with said remote $CO_2$ monitor; and
    said position optimizing the accuracy of $CO_2$ monitoring.

4. The face mask of claim 1, further comprising:
    a pair of posts mounted on said flange in transversely spaced apart relation to one another;
    said posts defining strap fasteners for a strap when a strap extends around said user's head and when opposite ends of said strap engage an associated post.

* * * * *